United States Patent
Chang et al.

(10) Patent No.: US 10,443,028 B2
(45) Date of Patent: Oct. 15, 2019

(54) CELL CULTURE APPARATUS

(71) Applicant: CHUNG-ANG UNIVERSITY INDUSTRY-ACADEMIC COOPERATION FOUNDATION, Seoul (KR)

(72) Inventors: Seung Hwan Chang, Seoul (KR); Ji Hun Bae, Seoul (KR)

(73) Assignee: CHUNG-ANG UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 142 days.

(21) Appl. No.: 15/521,811

(22) PCT Filed: Mar. 20, 2015

(86) PCT No.: PCT/KR2015/002724
§ 371 (c)(1),
(2) Date: Apr. 25, 2017

(87) PCT Pub. No.: WO2016/153082
PCT Pub. Date: Sep. 29, 2016

(65) Prior Publication Data
US 2018/0282680 A1    Oct. 4, 2018

(51) Int. Cl.
*C12M 1/42* (2006.01)
*C12M 1/02* (2006.01)
(Continued)

(52) U.S. Cl.
CPC .............. *C12M 35/02* (2013.01); *C12M 1/02* (2013.01); *C12M 1/14* (2013.01); *C12M 1/42* (2013.01);
(Continued)

(58) Field of Classification Search
CPC .............................. C12M 25/02; C12M 35/04
(Continued)

(56) References Cited

U.S. PATENT DOCUMENTS

| | | | | |
|---|---|---|---|---|
| 6,121,042 A | * | 9/2000 | Peterson | ................ C12M 41/00 435/284.1 |
| 2009/0053813 A1 | * | 2/2009 | Evans | .................. B01J 19/0046 435/461 |

FOREIGN PATENT DOCUMENTS

| | | |
|---|---|---|
| WO | 2008-135269 A1 | 11/2008 |
| WO | 2014-144219 A1 | 9/2014 |

OTHER PUBLICATIONS

Keplinger et al. "Stretchable, transparent, ionic conductors," Aug. 30, 2013, Science, vol. 341, pp. 984-987 and Supplemental Materials (Year: 2013).*
(Continued)

*Primary Examiner* — Kevin Joyner
*Assistant Examiner* — Holly M Mull
(74) *Attorney, Agent, or Firm* — Novick, Kim & Lee, PLLC; Sang Ho Lee

(57) ABSTRACT

Techniques for providing in vivo environments to in vitro cells by periodically applying mechanical stimuli to in vitro cells are provided for effective studies on cell culture. A first embodiment of the present invention provides a cell culture apparatus including: a first layer including an electroactive polymer material and elongated in at least one direction by external force applied thereto; a first fixing part fixing both ends of the first layer in the direction in which the first layer is elongated, so as to maintain the elongation of the first layer; a second layer including the electroactive polymer material and spaced apart from a surface of the first layer, the second layer being elongated in at least one direction by external force applied thereto; a second fixing part fixing both ends of the second layer in the direction in which the
(Continued)

second layer is elongated, so as to maintain the elongation of the second layer; a first electrode part applied to a region of the first layer; and a second electrode part applied to a region of the second layer, wherein the second layer is provided in such a manner that a cell to be cultured is sandwiched between the surface of the first layer and a surface of the second layer.

9 Claims, 7 Drawing Sheets

(51) Int. Cl.
  *C12M 3/04* (2006.01)
  *C12M 3/00* (2006.01)
  *C12M 1/14* (2006.01)
(52) U.S. Cl.
  CPC ............... *C12M 3/00* (2013.01); *C12M 3/04* (2013.01); *C12M 35/04* (2013.01)

(58) Field of Classification Search
  USPC ........................................................ 435/285.1
  See application file for complete search history.

(56) References Cited

OTHER PUBLICATIONS

Akbari, Arrays of dielectric elastomer microactuators for cell mechanotransduction, 2013, retrieved from Infoscience (EPFL scientific publications) (Year: 2013).*
Kam et al., Cell adhesion to protein-micropatterned-supported lipid bilayer membranes, Jun. 2001, Journal of Biomedical Materials Research, 55(4), pp. 487-495 (Year: 2001).*
Waters et al., A system to impose prescribed homogenous strains on cultured cells, 2001, Journal of Applied Physiology, vol. 91, 1600-1610 (Year: 2001).*
S. Akbari et al. "Microfabrication and characterization of an array of dielectric elastomer actuators generating uniaial strain to stretch individual cells" Journal of Micromechanics and Microengineering, vol. 22, pp. 1-12 (2012).

* cited by examiner

CELL CULTURE APPARATUS

TECHNICAL FIELD

The present invention relates to techniques for effectively culturing cells or tissues by applying mechanical stimuli to the cells or tissues, and more particularly, to techniques for applying static and dynamic loads to in vitro cells like in an in vivo environment and effectively applying mechanical stimuli to cells and tissues.

BACKGROUND ART

In general, research into cells and tissues has been conducted by placing cells to be cultured in a culture apparatus and then simulating the cells or analyzing natural culture processes of the cells.

However, cells in living bodies in which activities of cellular tissues actually occur are subjected to very active mechanical stimuli. Therefore, the influence of mechanical stimuli on the behavior and growth of cells and tissues has to be experimentally investigated for efficient research into the state of culture of cells. However, it is very difficult to perform such experiments in an in vitro environment using current cell culture systems.

In the related art, various techniques for applying various mechanical stimuli to cells in vitro have been used to address the above-mentioned problems. For example, methods such as applying a negative pressure to the inside of a micropipette, applying mechanical stimuli using magnetic beads and magnets, applying mechanical stimuli by introducing a fluid, or contracting and relaxing a flexible plate by applying external force to the flexible plate have been used for cell culture.

However, since apparatuses for such methods usually have centimeter-sized areas, it is difficult to observe and analyze single-cell differentiation and culture using the apparatuses. Therefore, it is difficult to precisely analyze cell differentiation using the apparatuses.

DETAILED DESCRIPTION OF THE INVENTION

Technical Problem

An object of the present invention is to provide techniques for precisely analyzing culture procedures of a single cell as well as culture procedures of a large tissue and providing an in vivo environment to in vitro cells by periodically applying mechanical stimuli to the cells, for effective studies on cell culture.

Technical Solution

Accordingly, a first embodiment of the present invention provides a cell culture apparatus including: a first layer including an electroactive polymer material and elongated in at least one direction by external force applied thereto; a first fixing part fixing both ends of the first layer in the direction in which the first layer is elongated, so as to maintain the elongation of the first layer; a second layer including the electroactive polymer material and spaced apart from a surface of the first layer, the second layer being elongated in at least one direction by external force applied thereto; a second fixing part fixing both ends of the second layer in the direction in which the second layer is elongated, so as to maintain the elongation of the second layer; a first electrode part applied to a region of the first layer; and a second electrode part applied to a region of the second layer, wherein the second layer is provided in such a manner that a cell to be cultured is sandwiched between the surface of the first layer and a surface of the second layer.

A second embodiment of the present invention provides a cell culture apparatus including: a main layer including an electroactive polymer material and elongated in at least one direction by external force applied thereto; a fixing part fixing both ends of the main layer in the direction in which the main layer is elongated, so as to maintain the elongation of the main layer; and an electrode part applied to a region of the main layer, wherein a pattern part is formed on one of both surfaces of the main layer on which a cell to be cultured is placed.

A third embodiment of the present invention provides a cell culture apparatus including: a main layer including an electroactive polymer material and elongated in at least one direction by external force applied thereto, the main layer including a pattern part formed on one of both surfaces of the main layer on which a cell to be cultured is placed; a fixing part fixing one of both ends of the main layer in the direction in which the main layer is elongated, so as to maintain the elongation of the main layer; a supporting part provided on a surface of the main layer and supporting the main layer; and an electrode part applied to a region of the main layer, wherein the other end of both ends of the main layer opposite the end of the main layer fixed by the fixing part is fixed to the supporting part.

Advantageous Effects of the Invention

According to first and second embodiments of the present invention, an electrode is applied to an electroactive polymer material, and voltage is applied to the electrode after fixing two or one layer of the electroactive polymer material in an elongated state. Therefore, a portion of the layer on which a cell is placed may be markedly deformed by several tens of percents (%), and a shearing mechanical stimulus may be periodically applied to the cell according to the structure of the layer. That is, behaviors like those of living body muscles may be induced, and environments similar to living body tissues may be obtained, thereby making it possible to provide techniques for experimentally studying the differentiation and development of cells in an in vitro environment based on a mechano-regulation theory.

According to a third embodiment of the present invention, an electrode is applied to an electroactive polymer material, and voltage is applied to the electrode after elongating a main layer of the electroactive polymer material, fixing an end of the main layer, and supporting the main layer using a supporting part to prevent the main layer from being bent in a natural state. Therefore, a portion of the main layer on which a cell is placed may be markedly deformed by several tens of percents (%), and a shearing mechanical stimulus may be periodically applied to the cell according to the structure of the main layer. That is, behaviors like those of living body muscles may be induced, and environments similar to living body tissues may be obtained, thereby making it possible to provide techniques for experimentally studying the differentiation and development of cells in an in vitro environment based on a mechano-regulation theory.

In addition, a micro-sized pattern may be formed on a surface of an electroactive polymer material layer. Thus, a shearing mechanical stimulus may be applied to cells owing to asymmetry of the layer, and it is possible to bring cells

BEAST MODE

Figure 1:
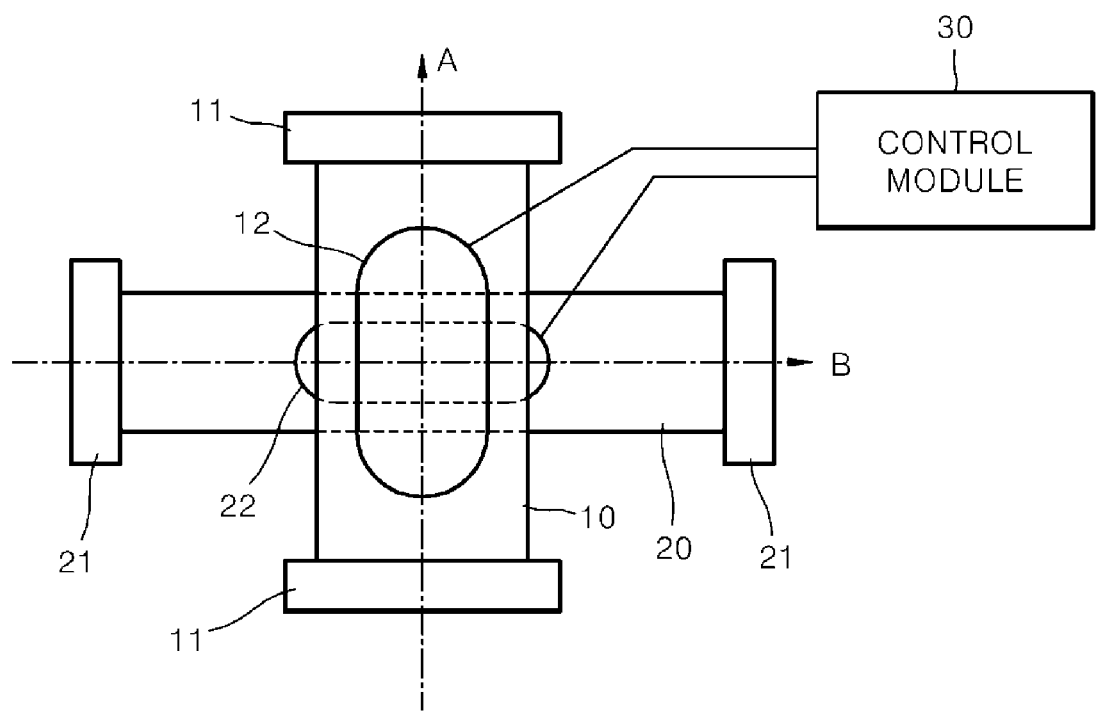
FIG. 1 is a schematic plan view illustrating a cell culture apparatus according to a first embodiment of the present invention.

Hereinafter, cell culture apparatuses will be described according to embodiments of the present invention with reference to the accompanying drawings. In FIGS. 1 to 14, the thicknesses, sizes, and shapes of layers, pattern parts, and cells are illustrated in such a manner that the description of the present invention will be easily understood. However, it will be apparent that the layers, pattern parts, and cells actually have micrometer-scale structures.

In addition, although descriptions of first to third embodiments of the present invention may be overlapped with each other, these embodiments can be implemented independent of each other, and elements indicated with different reference numerals or introduced in different embodiments may be understood as different technical elements even though the elements have the same name.

First Embodiment

FIG. 1 is a schematic plan view illustrating a cell culture apparatus according to a first embodiment of the present invention.

Referring to FIG. 1, the cell culture apparatus of the first embodiment of the present invention includes: a first layer 10 including an electroactive polymer material and elongated in at least one direction A by external force applied thereto; a first fixing part 11 fixing both ends of the first layer 10 in the direction A in which the first layer 10 is elongated, so as to maintain the elongation of the first layer 10 in the direction A; and a first electrode part 12 applied to a region of the first layer 10.

In addition, the cell culture apparatus includes: a second layer 20 including an electroactive polymer material and spaced apart from a surface of the first layer 10 (a lower surface of the first layer 10 in FIG. 1), the second layer 20 being elongated in at least one direction B by external force applied thereto; a second fixing part 21 functioning like the first fixing part 11, that is, the second fixing part 21 fixing both ends of the second layer 20 in the direction B in which the second layer 20 is elongated, so as to maintain the elongation of the second layer 20; and a second electrode part 22 applied to a region of the second layer 20.

In this structure, cells or tissue is placed between the first and second layers 10 and 20. That is, the first and second layers 10 and 20 may be disposed such that cells may be sandwiched between surfaces of the first and second layers 10 and 20.

In addition, the first electrode part 12 and the second electrode part 22 may be applied in such a manner that the first electrode part 12 and the second electrode part 22 are insulated from the surfaces on which cells are placed. This is because cells may necrotize when a voltage applied to the first and second electrode parts 12 and 22 is transmitted to the cells.

The first and second layers 10 and 20 may include an electroactive polymer material. If an electric stimulus is applied to the electroactive polymer material, the electroactive polymer material varies in size at a ratio of several tens of percents. In this case, an electrode-coated portion is compressed in a thickness direction by Maxwell's force, and since the electroactive polymer material is an incompressible material, the electrode-coated portion may be elongated in a surface direction.

As described above, the first and second fixing parts 11 and 21 have a function of fixing the first and second layers 10 and 20 in an elongated state in the directions A and B, respectively. When the electroactive polymer material is applied to the cell culture apparatus in form of the first and second layers 10 and 20, the first and second layers 10 and 20 may be configured to have very small thicknesses (in micrometers). Therefore, if the first and second layers 10 and 20 are not fixed, the first and second layers 10 and 20 may not be maintained flat, that is, may droop because of gravity.

In addition, it is necessary to maintain the electroactive polymer material in a previously elongated state so as to increase the deformation ratio of the electroactive polymer material and guarantee lasting stable behavior of the electroactive polymer material.

For these two purposes, the first and second fixing parts 11 and 21 have a function of maintaining the first and second layers 10 and 20 in an elongated state, respectively.

In a specific implementation example of the first embodiment of the present invention, the first and second electrode parts 12 and 22 may be different from each other in at least one of the sizes of the regions to which the first and second electrode parts 12 and 22 are applied and the patterns of the first and second electrode parts 12 and 22, so as to cause the first and second layers 10 and 20 to deform in different directions by different amounts and thus to efficiently apply mechanical stimuli to cells.

In addition, the first and second layers 10 and 20 may be different from each other in at least one of area and thickness.

As described above, the electroactive polymer material deforms when voltage is applied to electrode-coated regions thereof. In this case, if the electrode-coated regions have different sizes, the electroactive polymer material may deform at different ratios in the electrode-coated regions. That is, the first and second layers 10 and 20 may deform at different ratios, and thus relatively large mechanical stimuli may be applied to cells.

In addition, electrodes applied in different patterns may result in deformation at different ratios or in different directions, that is, different deformation behaviors of the first and second layers 10 and 20, thereby making it possible to apply relatively large mechanical stimuli to cells.

In addition, the first and second layers 10 and 20 may differently deform if the first and second layers 10 and 20 are different from each other in at least one of area and thickness.

Referring to FIG. 1, the first and second layers 10 and 20 are elongated in different directions A and B. If voltage is applied to the first and second electrode parts 12 and 22 in a state in which the first and second layers 10 and 20 are respectively elongated in the directions A and B as shown in FIG. 1, the electrode-coated region of the first layer 10 and the electrode-coated region of the second layer 20 may undergo different shear deformations. In this case, relatively large mechanical stimuli may be applied to cells compared to the case of simple deformation, and thus mechanical stimuli may be more efficiently applied to cells.

A control module 30 applies voltage to the first and second electrode parts 12 and 22 while controlling at least one of the amplitude, frequency, and phase of the voltage.

That is, the control module 30 may adjust voltages applied to the first and second electrode parts 12 and 22 to be different in at least one of amplitude, frequency, and phase, so as to differently deform the first and second layers 10 and 20 and thus to efficiently apply mechanical stimuli to cells as described above.

As described above, electrode-coated portions of the electroactive polymer material deform in response to voltage applied thereto. Therefore, if voltages of different magnitudes and types are applied to the first and second layers 10 and 20, the first and second layers 10 and 20 may be deformed by different amounts in different directions. In this manner, different deformations may occur even though layer structures or electrode coatings are not varied. In addition to this, if layer structures or electrode coatings are varied, different deformations may be more efficiently induced.

In detail, the control module 30 may apply voltages having different phases to the first and second electrode parts 12 and 22 so as to cause cells or tissue placed between the first and second layers 10 and 20 to undergo shear deformation.

Voltages of different phases may cause the electrode-coated portions of the electroactive polymer material to deform in different directions. The deformations occurring in different directions may cause cells or tissue placed between the first and second layers 10 and 20 to undergo shear deformation. In this case, the cells sandwiched between the first and second layers 10 and 20 may be subjected to a large mechanical stimulus (shear deformation) because the first and second layers 10 and 20 deform by different amounts in different directions.

In this manner, the electrode-coated regions of the first and second layers 10 and 20 including the electroactive polymer material may be deformed in different directions or different forms so as to apply a large mechanical stimulus to the cells placed between the first and second layers 10 and 20. In addition, since mechanical stimuli are induced by applying voltage, if the voltage is controlled, periodic stimuli may be induced, and the amount and direction of deformation may be adjusted. Therefore, a custom-made cell culture apparatus capable of providing a cell-friendly environment by simulating complex, various bio-mechanisms according to the size and type of cells may be provided.

Figure 2:
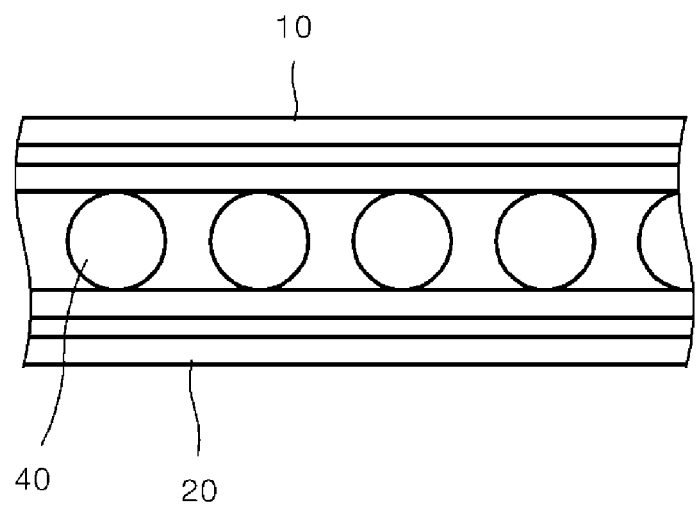
FIG. 2 is a side cross-sectional view illustrating layer structures according to the first embodiment of the present invention.

FIG. 2 is a side cross-sectional view illustrating layer structures according to the first embodiment of the present invention.

Referring to FIG. 2, cells 40 are sandwiched between the first and second layers 20. Each of the first and second layers 10 and 20 has a multi-layer structure.

Since each of the first and second layers 10 and 20 has a multi-layer structure, although low voltage is applied to the first and second layers 10 and 20, the first and second layers 10 and 20 may deform more than single-layer-structure layers having the same thickness as the first and second layers 10 and 20, thereby improving the efficiency of the cell culture apparatus.

In this case, the first and second layers 10 and 20 of the first embodiment of the present invention may have different layer structures so as to induce different deformation behaviors. That is, the layer structures of the first and second layers 10 and 20 may be set in such a manner that the region of the first layer 10, that is, the electrode-coated region of the first layer 10 in which deformation occurs may have a deformation ratio different from a deformation ratio of the electrode-coated region of the second layer 20 in which deformation occurs. Owing to this, mechanical stimuli may be more efficiently applied to the cells 40 as described above with reference to FIG. 1.

In detail, the number of layers of the first layer 10 may be set to be different from the number of layers of the second layer 20 such that the electrode-coated regions of the first and second layers 10 and 20 may deform at different ratios in response to the same voltage.

In another embodiment, the number of layers of the first layer 10 including the electroactive polymer material may be set to be different from the number of layers of the second layer 20 including the electroactive polymer material such that the electrode-coated regions of the first and second layers 10 and 20 may deform at different ratios in response to the same voltage.

As described above, the first and second layers 10 and 20 may be configured to have different hardware structures, that is, different layer structures such that the first and second layers 10 and 20 may have different deformation behaviors in response to the same voltage. Owing to this, the cells 40 may be efficiently stimulated.

Figure 3:
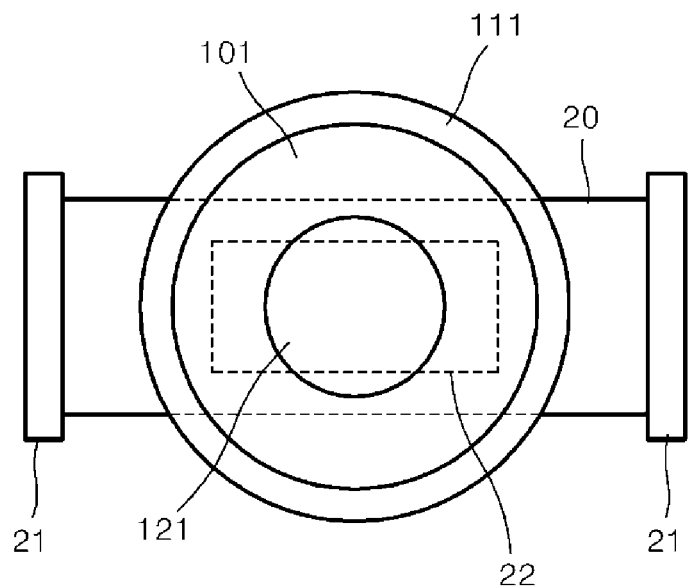
FIG. 3 is a plan view illustrating layer structures according to another implementation example of the first embodiment of the present invention.

FIG. 3 is a plan view illustrating layer structures according to another implementation example of the first embodiment of the present invention.

Referring to the example shown in FIG. 3, layer structures different from the layer structures shown in FIG. 1 are illustrated.

In FIG. 1, each of the first and second layers 10 and 20 has a rectangular shape and is fixed in a state in which the layer is elongated in one direction. In FIG. 3, however, a first layer 101 has a circular shape.

The first layer 101 having a circular shape is elongated in all directions. To this end, a first fixing part 111 having a ring shape maintains the first layer 101 in a state in which the first layer 101 is elongated in all directions. Referring to FIG. 3, a first electrode part 121 is applied to the first layer 101 in a circular shape. However, the pattern and shape of the first electrode part 121 may vary as described above.

Like in FIG. 1, a second layer 20 is elongated in one direction and fixed by a second fixing part 21, and a second electrode part 22 is applied to the second layer 20.

In the embodiment shown in FIG. 3, cells may be placed between the first and second layers 101 and 20, and the first and second layers 101 and 20 may be deformed in different forms. That is, the embodiment in FIG. 3 shows that the shapes and elongation directions of layers may vary so as to more efficiently stimulate cells.

That is, according to various embodiments of the present invention, the shapes and elongation directions of layers, the shapes of fixing parts, and the shapes, sizes, and patterns of electrodes may be variously selected so as to provide structures for culturing various cells.

Figure 4:
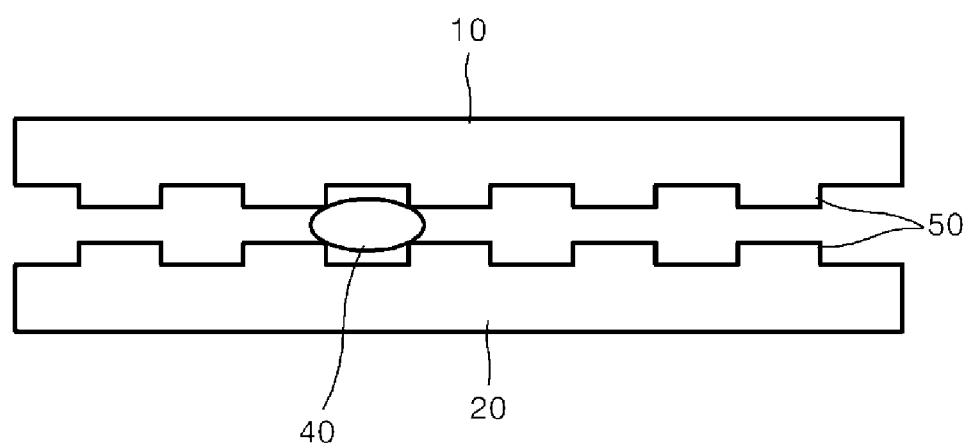
FIG. 4 is a side cross-sectional view illustrating layer structures according to another implementation example of the first embodiment of the present invention.

FIG. 4 is a side cross-sectional view illustrating layer structures according to another implementation example of the first embodiment of the present invention.

Referring to FIG. 4, pattern parts 50 are formed on surfaces of first and second layers 10 and 20 on which a cell 40 to be cultured is placed, and the pattern parts 50 has a concave-convex structure according to the size of the cell 40.

It is necessary to bring the cell 40 into tight contact with a surface undergoing mechanical deformation so as to efficiently apply mechanical stimuli to the cell 40. To this end, the pattern parts 50 are provided to fix the cell 40 to the surfaces of the first and second layers 10 and 20. The pattern parts 50 may have a concave-convex structure or a ridge-valley structure, and the patterns and sizes of the pattern parts 50 may vary according to the cell 40.

As well as the pattern parts 50 having contact and fixing functions for cells, the pattern parts 50 have a function of imparting asymmetry to the structures of the first and second layers 10 and 20 such that the first and second layers 10 and 20 may undergo not only thickness-wise compression and widthwise elongation but also vertical deformation, that is, bending. Thus, more diverse mechanical stimuli may be applied to the cell 40.

To this end, the pattern parts 50 of the first and second layers 10 and 20 may have different concave-convex structures. That is, the pattern parts 50 may have different concave-convex patterns, different concave-concave structure sizes, or the like, so as to induce various deformations.

Figure 5:
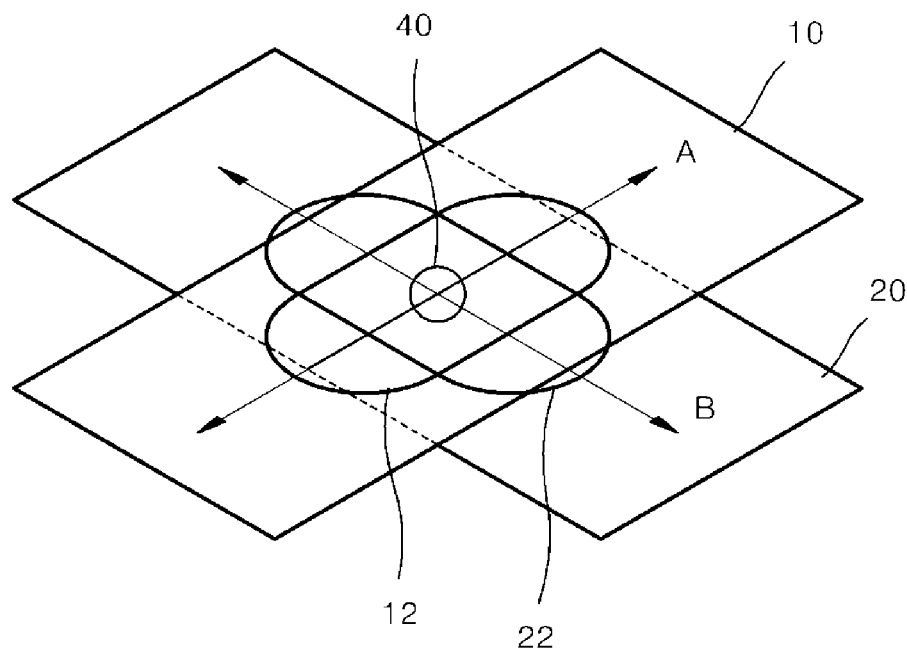
FIG. 5 is a perspective view illustrating directions of layer behaviors according to an implementation example of the first embodiment of the present invention.
Figure 6:
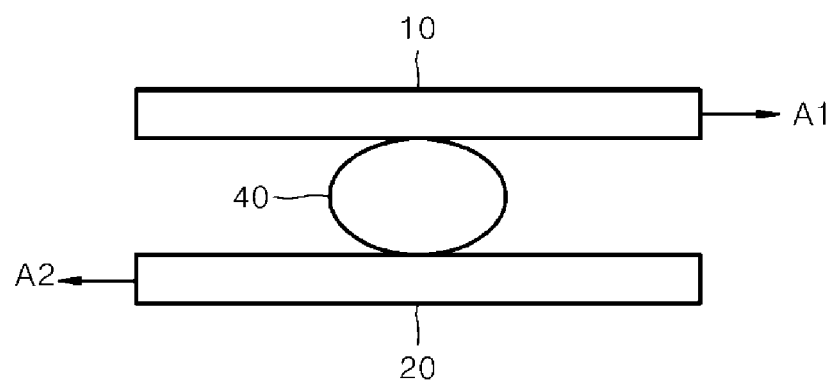
FIG. 6 is a side cross-sectional view illustrating directions of layer behaviors according to another implementation example of the first embodiment of the present invention.

FIG. 5 is a perspective view illustrating directions of layer behaviors according to an implementation example of the first embodiment of the present invention, and FIG. 6 is a side cross-sectional view illustrating directions of layer behaviors according to another implementation example of the first embodiment of the present invention. The same descriptions as those given with reference to FIGS. 1 to 4 will not be repeated in the following description.

Referring to FIG. 5, first and second layers 10 and 20 are placed with a cell 40 therebetween. The first and second layers 10 and 20 are coated with first and second electrode parts 12 and 22 as described above, and thus if voltage is applied to electrode-coated regions of the first and second layers 10 and 20, the first and second layers 10 and 20 are deformed.

In this case, the first and second layers 10 and 20 are configured to be elongated in directions A and B, respectively, and thus a stimulus causing shear deformation may be applied to the cell 40.

Referring to FIG. 6, a first layer 10 may deform in a direction A1, and a second layer 20 may deform in a direction A2. Then, a stimulus causing shear deformation may be applied to a cell 40. The example shown in FIG. 6 may be implemented by varying the phase of voltage, for example, using a control module as described above.

Second Embodiment

The same descriptions as those given with reference to FIGS. 1 to 6 will not be repeated in the following description.

Figure 7:
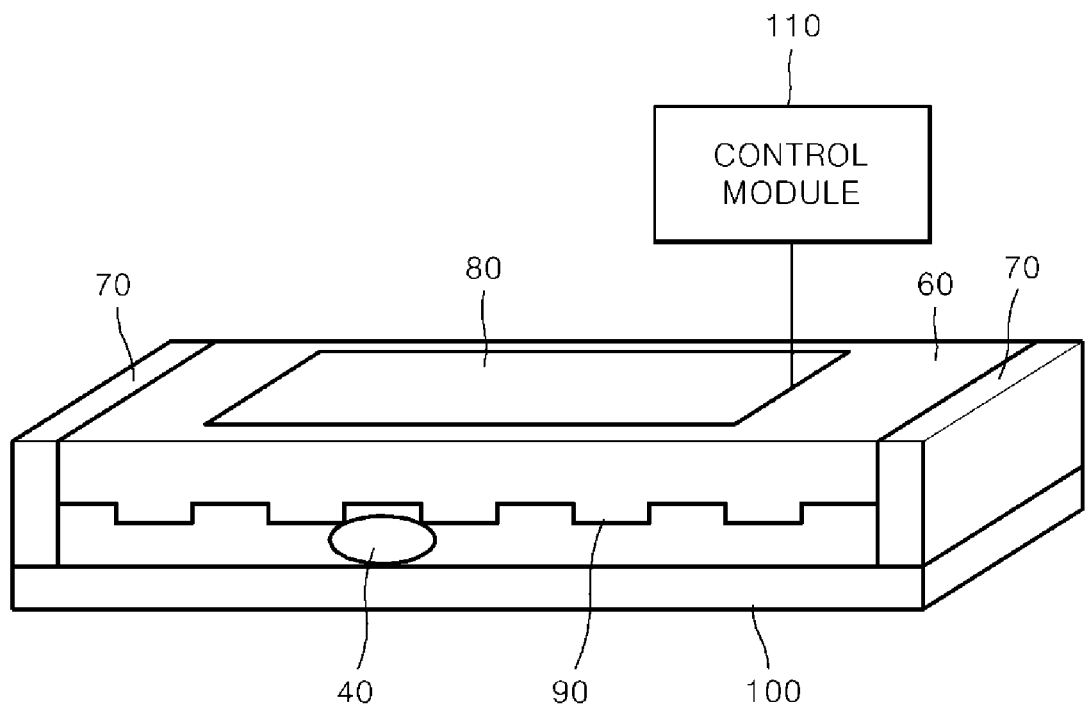
FIG. 7 is a schematic perspective view illustrating a cell culture apparatus according to a second embodiment of the present invention.

FIG. 7 is a schematic perspective view illustrating a cell culture apparatus according to a second embodiment of the present invention.

Referring to FIG. 7, according to the second embodiment of the present invention, the cell culture apparatus includes: a main layer 60 including an electroactive polymer material and elongated in at least one direction by external force; a fixing part 70 fixing both ends of the main layer 60 in the direction in which the main layer 60 is elongated, so as to maintain the elongation of the main layer 60; and an electrode part 80 applied to a region of the main layer 60.

In this structure, as described above, a pattern part 90 may be formed on one of both surfaces of the main layer 60 on which a cell 40 to be cultured is placed.

The second embodiment of the present invention is different from the first embodiment in that a layer formed of an electroactive polymer material is only the main layer 60. In the second embodiment of the present invention, that is, the cell 40 is mechanically stimulated as the main layer 60 deforms.

Like in the first embodiment, the main layer 60 may have a structure in which a plurality of layers are stacked, and all or some of the plurality of layers may be formed of the electroactive polymer material.

In addition, the pattern part 90 may have a ridge-valley structure sized according to the size of the cell 40. Owing to the pattern part 90, the cell 40 may be fixed to the main layer 60 and may be more efficiently mechanically stimulated according to deformation of the main layer 60, and at the same time, it is possible to impart asymmetry to the main layer 60 and deform the main layer 60 in various forms.

In addition, referring to FIG. 7, a sub-layer 100 is provided. The sub-layer 100 is spaced apart from one of both surfaces of the main layer 60 on which the cell 40 is placed such that the cell 40 may be sandwiched between the main layer 60 and the sub-layer 100.

Like the main layer 60, the sub-layer 100 has a structure in which at least one layer is arranged, and unlike the main layer 60, the sub-layer 100 may include a material other than an electroactive polymer material. That is, the sub-layer 100 functions as a support for the cell 40.

In another implementation example of the second embodiment of the present invention, the sub-layer 100 may not be used. In this case, preferably, the cell 40 may be placed on an upper portion of the main layer 60, and the pattern part 90 may be formed on the upper portion of the main layer 60.

Like in the first embodiment, a control module 110 may be used to control the amplitude and frequency of voltage applied to the electrode part 80 and thus to simulate more diverse in vivo conditions.

The control module 110 may set the amplitude and frequency of voltage applied to the electrode part 80 so as to control the thickness-area deformation ratio and deformation frequency of the main layer 60 according to the cell 40 to be cultured.

Figure 8:
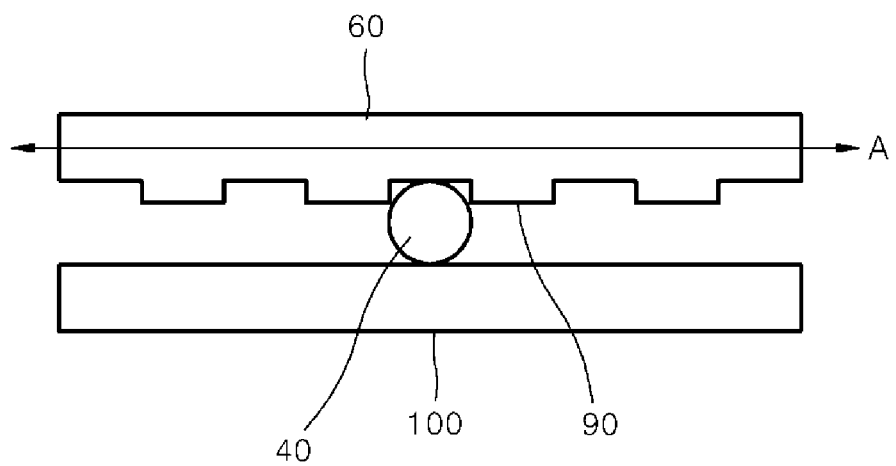
FIG. 8 is a side cross-sectional view illustrating a first behavior of layers according to an implementation example of the second embodiment of the present invention.
Figure 9:
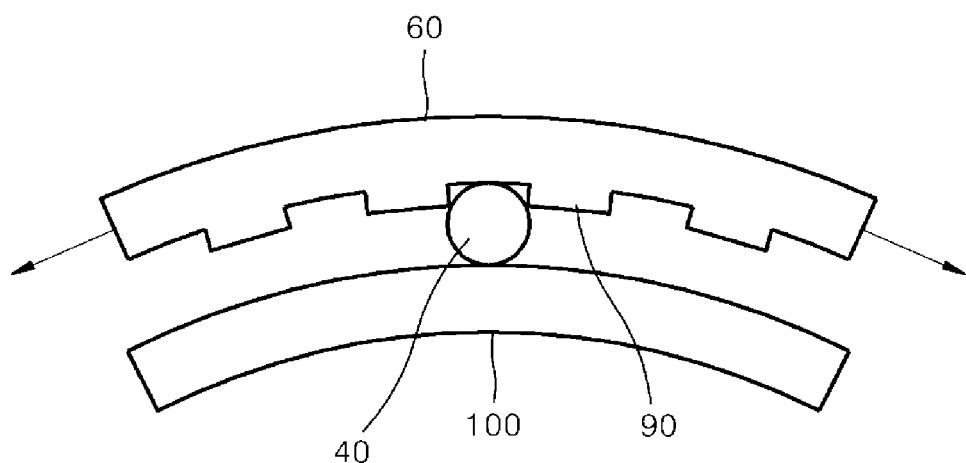
FIG. 9 is a side cross-sectional view illustrating a second behavior of layers according to an implementation example of the second embodiment of the present invention.

FIG. 8 is a side cross-sectional view illustrating a first behavior of layers according to an implementation example of the second embodiment of the present invention, and FIG. 9 is a side cross-sectional view illustrating a second behavior of layers according to an implementation example of the second embodiment of the present invention.

Referring to FIG. 8, a cell 40 is placed between the sub-layer 100 and the main layer 60, and the pattern part 90 formed on a lower portion of the main layer 60 fixes the cell 40 and imparts asymmetry to the main layer 60.

Unlike in the first embodiment, the main layer 60 may deform in one direction A in response to voltage.

At this time, the main layer 60 may deform upward and downward according to a stack structure of the main layer 60 and the pattern part 90 as shown in FIG. 9. Referring to FIG. 9, the main layer 60 undergoes vertical deformation together with side-to-side deformation, resulting in bending of the main layer 60 and the sub-layer 100. The cell 40 may be stimulated in more diverse directions according to the bending of the main layer 60. In FIG. 9, for ease of illustration, the sub-layer 100 is illustrated as being bent. However, for example, the cell 40 placed between the main layer 60 and the sub-layer 100 may undergo shear deformation because of different deformations of the main layer 60 and the sub-layer 100 tending to maintain its flat state.

Third Embodiment

Figure 10:
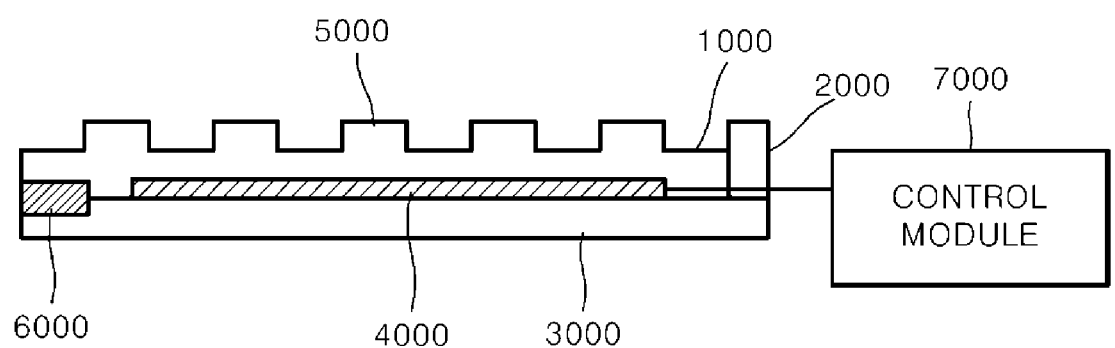
FIG. 10 is a side cross-sectional view illustrating a cell culture apparatus according to a third embodiment of the present invention.

FIG. 10 is a schematic plan view illustrating a cell culture apparatus according to a third embodiment of the present invention.

Referring to FIG. 10, according to the third embodiment of the present invention, the cell culture apparatus includes a main layer 1000 including an electroactive polymer material and elongated in at least one direction by external force, and a pattern part 5000 is formed on one of both surfaces of the main layer 1000 on which a cell to be cultured is placed.

In addition, the cell culture apparatus includes: a fixing part 2000 fixing one of both ends of the main layer 1000 in the direction in which the main layer 1000 is elongated, so as to maintain the elongation of the main layer 1000; and a supporting part 3000 contacting a surface of the main layer 1000 or facing the surface of the main layer 1000 with a gap therebetween so as to support the main layer 1000.

For example, as shown in FIG. 10, an insulation structure separating an electrode part 4000 from a region in which the cell is placed may be provided so as to prevent necrosis of the cell caused by an electric stimulus.

The electrode part 4000 may be applied to both surfaces of the main layer 1000, and when voltage is applied to regions in which the electrode part 4000 is applied, deformation may occur because of characteristics of the electroactive polymer material.

The other end of the main layer 1000 opposite to the end of the main layer 1000 fixed by the fixing part 2000 may be fixed by the supporting part 3000 so as to maintain the elongation of the main layer 1000. According to an embodiment of the present invention, the supporting part 3000 and the main layer 1000 may be fixed by a fixing means 6000.

The fixing means 6000 may include an adhesive for chemically fixing the supporting part 3000 and the main layer 1000 to each other or a part such as a pin or clip for mechanically fixing the supporting part 3000 and the main layer 1000 to each other.

The main layer 1000 includes the electroactive polymer material. If an electric stimulus is applied to the electroactive polymer material, the electroactive polymer material varies in size at a ratio of several tens of percents. In this case, an electrode-coated portion of the electroactive polymer material may be compressed in a thickness direction by Maxwell's force, and since the electroactive polymer material is an incompressible material, the electrode-coated portion may be elongated in a surface direction.

The main layer 1000 of the cell culture apparatus including the electroactive polymer material may have a very small thickness (in micrometers). Therefore, if the main layer 1000 is not supported, when voltage is not applied to the main layer 1000, the main layer 1000 may not be maintained flat because of gravity, that is, the main layer 1000 may be bent downward, and thus a cell may not be properly supported by the main layer 1000.

In addition, it is necessary to maintain the electroactive polymer material in a previously elongated state so as to increase the deformation ratio of the electroactive polymer material and guarantee lasting stable behavior of the electroactive polymer material.

To achieve the two purposes, the end of the main layer 1000 is fixed to the fixing part 2000, and the supporting part 3000 supports the main layer 1000 in a state in which an end of the supporting part 3000 opposite the end of the main layer 1000 fixed to the fixing part 2000 is coupled to the main layer 1000, thereby fixing the main layer 1000 in an elongated state.

In addition, when a control module 7000 applies voltage to the electrode part 4000, the control module 7000 controls at least one of the amplitude and frequency of the voltage.

As described above, an electrode-coated portion of the electroactive polymer material deforms in response to voltage applied thereto. Therefore, if the amplitude and frequency of voltage applied to the main layer 1000 is controlled, a periodic stimulus may be applied to the main layer 1000, and the thickness-area deformation ratio and deformation period of the main layer 1000 may be easily controlled. Therefore, a custom-made cell culture apparatus capable of providing a cell-friendly environment by simulating complex, various bio-mechanisms according to the size and type of cells may be provided.

In addition, according to the third embodiment of the present invention, the shape and elongation direction of a layer, the shape of a fixing part, and the shape, size, and pattern of an electrode may be variously selected so as to provide structures for culturing various cells.

In addition, a pattern part 5000 is formed on one of both surfaces of the main layer 1000 on which a cell to be cultured will be placed. The pattern part 5000 may have a ridge-valley structure sized according to the size of the cell. Owing to this, the cell may be fixed to the main layer 1000 and may be more efficiently mechanically stimulated according to deformation of the main layer 1000, and at the same time, it is possible to impart asymmetry to the main layer 1000 and deform the main layer 1000 in various forms by applying voltage to the main layer 1000. To this end, the size and shape of the pattern part 5000 may be variously set.

In addition, the main layer 1000 may have a structure in which a plurality of layers are stacked, and all or some of the plurality of layers may be formed of the electroactive polymer material.

Unlike the main layer 1000, the supporting part 3000 may include a material other than an electroactive polymer material. In this case, the supporting part 3000 may have strength enough to maintain the main layer 1000 in a flat state when voltage is not applied to the electrode part 4000, and rigidity enough to maintain its shape when force is applied thereto, that is, when the main layer 1000 is bent in response to voltage applied to the electrode part 4000. In other embodiments of the present invention, the rigidity of the supporting part 3000 may be set such that when the main layer 1000 is bent in response to voltage applied to the electrode part 4000, the supporting part 3000 may also be bent.

In this structure, if voltage is applied to the electrode part 4000 after a cell is placed on the main layer 1000, the main layer 1000 maintained in a state in which the main layer 1000 is elongated by the fixing part 2000 and the fixing means 6000 may deform at a large deformation ratio. At this time, owing to asymmetry imparted to the main layer 1000 by the pattern part 5000, the main layer 1000 may deform in various forms. In addition, since the cell is fixed to and tightly brought into contact with the main layer 1000 owing the pattern part 5000, mechanical stimuli may be efficiently applied to the cell as the main layer 1000 deforms.

In addition, since the control module 7000 controls the amplitude and frequency of voltage, stimuli suitable for various cells may be generated, and thus cell culture conditions may be flexibly controlled.

Figure 11:
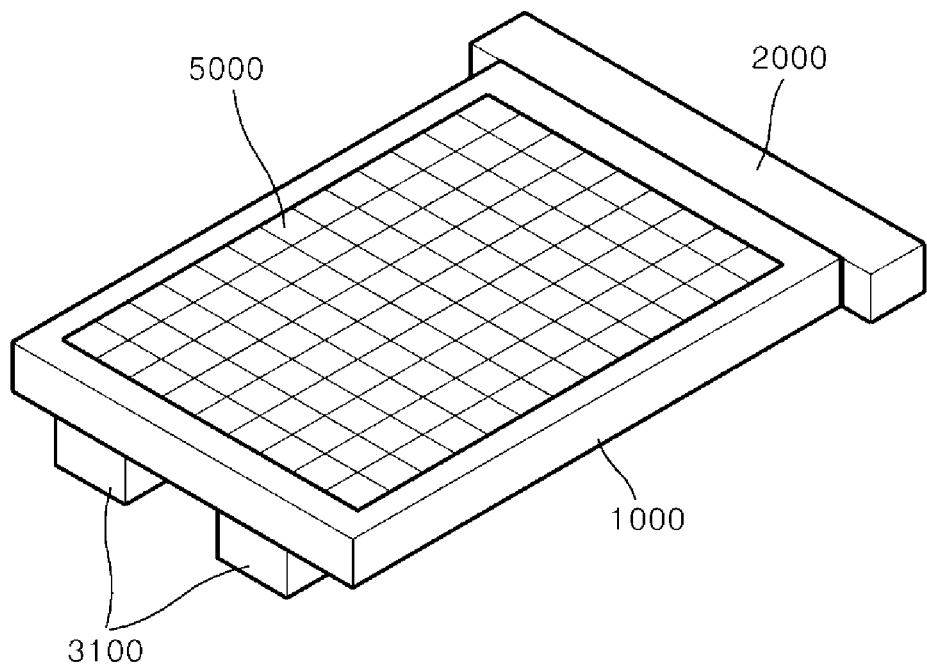
FIG. 11 is a perspective view illustrating a beam-shaped supporting part according to an implementation example of the third embodiment of the present invention.
Figure 12:
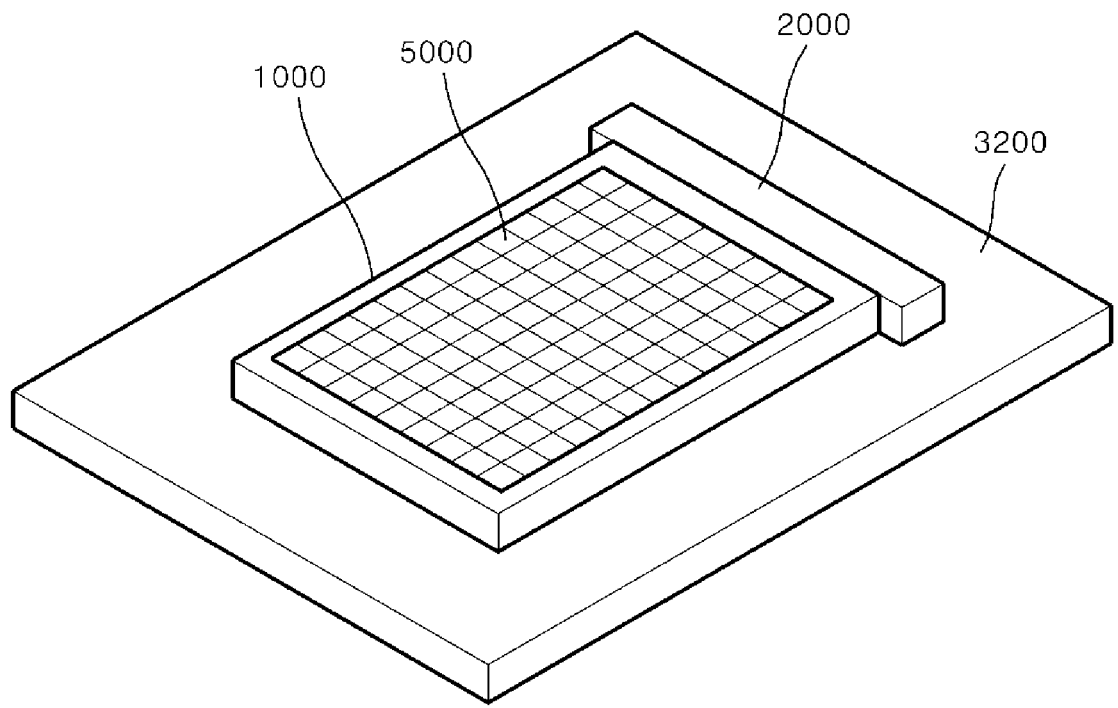
FIG. 12 is a perspective view illustrating a plate-shaped supporting part according to another implementation example of the third embodiment of the present invention.

FIG. 11 is a perspective view illustrating a beam-shaped supporting part according to an implementation example of the third embodiment of the present invention, and FIG. 12 is a perspective view illustrating a plate-shaped supporting part according to another implementation example of the third embodiment of the present invention.

Such supporting parts have a function of supporting the main layer 1000.

Referring to FIG. 11, a supporting part 3100 includes a plurality of beams. The supporting part 3100 may support a minimum area of the main layer 1000 to guarantee deformation of the main layer 1000.

As described above, an end of the main layer 1000 is fixed to the fixing part 2000, and the other end of the main layer 1000 is fixed to the supporting part 3100. In FIG. 11, the pattern part 5000 is illustrated as having a lattice pattern. However, the size and pattern of the pattern part 5000 may be varied according to cells to be cultured.

Referring to FIG. 12, a supporting part 3200 has a plate shape with an area equal to or greater than the area of the main layer 1000 maintained in an elongated state. The supporting part 3200 may maintain the main layer 1000 in a flat state and securely fix the main layer 1000 in a state in which voltage is not applied to the main layer 1000.

Like in FIG. 11, an end of the main layer 1000 is fixed to the fixing part 2000, and the other end of the main layer 1000 is fixed to the supporting part 3200. In FIG. 11, the pattern part 5000 is illustrated as having a lattice pattern. However, the size and pattern of the pattern part 5000 may be varied according to cells to be cultured.

Figure 13:
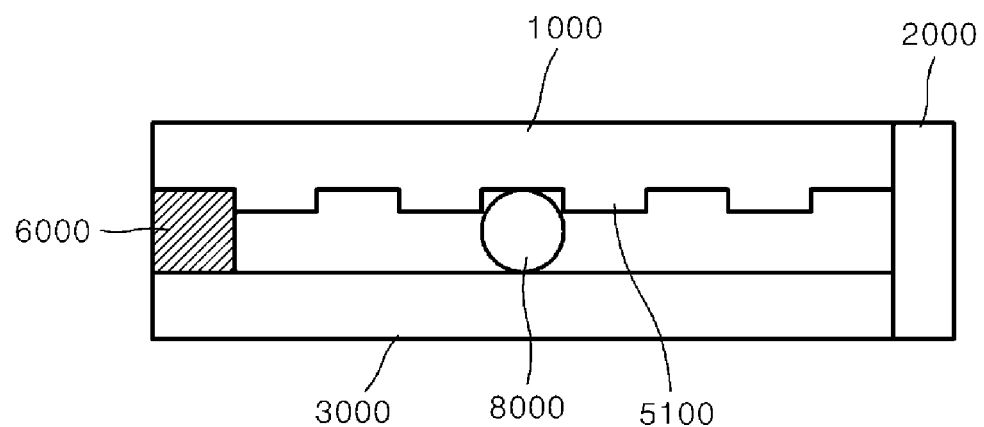
FIG. 13 is a side cross-sectional view illustrating a layer structure according to an implementation example of the third embodiment of the present invention.
Figure 14:
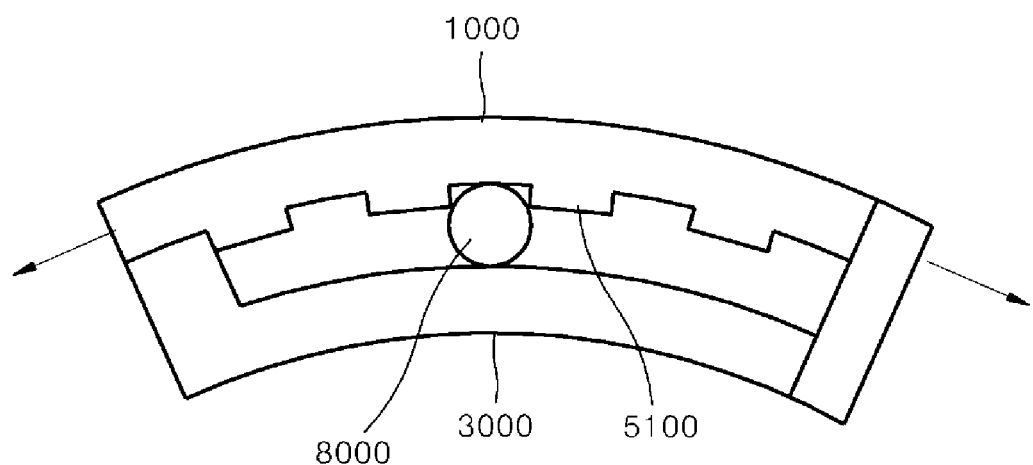
FIG. 14 is a side cross-sectional view illustrating deformation of a layer according to an implementation example of the third embodiment of the present invention.

FIG. 13 is a side cross-sectional view illustrating a layer structure according to an implementation example of the third embodiment of the present invention, and FIG. 14 is a side cross-sectional view illustrating deformation of a layer according to an implementation example of the third embodiment of the present invention.

First, referring to FIG. 13, a main layer 1000 is fixed by a fixing part 2000. In this case, unlike in FIG. 10, a cell 80 is placed between the main layer 1000 and a supporting part 3000. That is, in FIG. 10, the main layer 1000 is in contact with the supporting part 3000, and a cell to be cultured is placed on one of both surfaces of the main layer 1000 opposite the supporting part 3000. However, in FIG. 13, the cell 80 is placed between the main layer 1000 and the supporting part 3000.

Like in FIG. 10, an end of the main layer 1000 opposite to an end of the main layer 1000 fixed to the fixing part 2000 is fixed to the supporting part 3000 using a fixing means 6000. Like in FIG. 10, a pattern part 5100 may be formed on one of both surfaces of the main layer 1000 on which the cell 80 is placed. The pattern part 5100 shown in FIG. 13 also has a function of fixing the cell 8000 and a function of imparting asymmetry to the main layer 1000 in a thickness direction to induct various deformations of the main layer 1000.

In addition, a region of the main layer 1000 may be coated with an electrode, and voltage may be applied to the electrode.

The region of the main layer 1000 coated with the electrode may deform in response to voltage applied to the electrode, and thus the shape of the main layer 1000 may vary as shown in FIG. 14.

Referring to FIG. 14, for example, the main layer 1000 may be bent because of the asymmetry of the main layer 1000 imparted by the pattern part 5100. In this case, as described above, when the main layer 1000 is bent, the supporting part 3000 may maintain its shape or may also undergo bending deformation. In the example shown in FIG. 14, the supporting part 3000 is bent.

Referring to FIG. 14, like in FIG. 13, the fixing part (not indicated with a reference numeral) is on the right side of the main layer 1000, and the left side of the main layer 1000 may be fixed to the supporting part 3000.

In the above descriptions of the embodiments, although all the elements are described as being combined as one entity or operating in combination, the present invention is not limited to the embodiments. For example, all the elements may be selectively combined as at least one entity and may then be operated within the scope of the present invention.

Furthermore, in the above description, the terms "comprises," "constituted by" and/or "have" specify the presence of stated elements, but do not preclude the presence or addition of one or more other elements unless otherwise specified. Unless defined otherwise, all terms used herein, including technical and scientific terms, have the same meanings as those commonly understood by those skilled in the art to which the present invention pertains. Terms such as those defined in a generally used dictionary may be interpreted to have the same meanings as the contextual meanings in the relevant field of art, and are not to be interpreted to have ideal or excessively formal meanings unless clearly defined herein.

The above description of the present invention is for illustrative purposes only, and it will be apparent to those skilled in the art that modifications and variations could be made without departing from the scope of the present invention. That is, the embodiments of the present invention are for illustrative purposes only and are not intended to limit the scope of the present invention. Therefore, the scope of the present invention should be construed according to the appended claims, and it should be understood that all technical ideas equivalent to those described above are within the scope of the present invention.

The invention claimed is:

1. A cell culture apparatus comprising:
a first layer comprising an electroactive polymer material and elongated in at least one direction by external force applied thereto;
a first fixing part fixing both ends of the first layer in a first direction in which the first layer is elongated and maintaining an elongation orientation of the first layer;
a second layer comprising the electroactive polymer material and spaced apart from a surface of the first layer, the second layer being elongated in at least one direction by external force applied thereto;
a second fixing part fixing both ends of the second layer in a second direction in which the second layer is elongated and maintaining an elongation orientation of the second layer;
a first electrode part applied to a region of the first layer;
a second electrode part applied to a region of the second layer and,
a control module configured to adjust voltage applied to the first and second electrode parts to be different in at least one of amplitude, frequency, and phase, the first layer and the second layer having different deformation sizes and directions from one another,
wherein the first direction and the second direction are different from one another,
wherein a cell to be cultured is interposed between the surface of the first layer and a surface of the second layer, and
wherein at least one of elongation orientation, shape, and area of the first layer and the second layer are different from one another.

2. The cell culture apparatus of claim 1, wherein when the voltage is applied to the first electrode part and the second electrode part, a size deformation ratio of the region of the first layer to which the first electrode part is applied is different from a size deformation ratio of the region of the second layer to which the second electrode part is applied.

3. The cell culture apparatus of claim 2, wherein a number of layers stacked in the first layer is different from a number of layers stacked in the second layer, and when the voltage is applied to the first electrode part and the second electrode part, the size deformation ratio of the region of the first layer to which the first electrode part is applied is different from the size deformation ratio of the region of the second layer to which the second electrode part is applied.

4. The cell culture apparatus of claim 2, wherein a number of layers which include the electroactive polymer material and are stacked in the first layer is different from a number of layers, which include the electroactive polymer material and are stacked in the second layer, and when the voltage is applied to the first electrode part and the second electrode part, the size deformation ratio of the region of the first layer to which the first electrode part is applied is different from the size deformation ratio of the region of the second layer to which the second electrode part is applied.

5. The cell culture apparatus of claim 1, wherein at least one of sizes and patterns of the first electrode part and the second electrode part are different from one another.

6. The cell culture apparatus of claim 1, wherein the first layer and the second layer have different thickness.

7. The cell culture apparatus of claim 1, wherein the first layer and the second layer have different concave-convex patterns from one another.

8. The cell culture apparatus of claim 1, wherein the control module has a configuration to have different shear deformation of the first layer and the second layer by adjusting the voltage in different phase.

9. A cell culture apparatus comprising:
a first layer comprising an electroactive polymer material and elongated in at least one direction by external force applied thereto;
a first fixing part fixing both ends of the first layer in a first direction in which the first layer is elongated and maintaining an elongation orientation of the first layer;
a second layer comprising the electroactive polymer material and spaced apart from a surface of the first layer, the second layer being elongated in at least one direction by external force applied thereto;
a second fixing part fixing both ends of the second layer in a second direction in which the second layer is elongated and maintaining an elongation orientation of the second layer;
a first electrode part applied to a region of the first layer; and
a second electrode part applied to a region of the second layer,
wherein the first direction and the second direction are different from one another,
wherein a cell to be cultured is interposed between the surface of the first layer and a surface of the second layer, and
wherein at least one of shape, and area of the first layer and the second layer are different from one another.

* * * * *